United States Patent
Kuk et al.

(10) Patent No.: US 10,258,260 B2
(45) Date of Patent: Apr. 16, 2019

(54) METHOD OF TESTING HEARING AND A HEARING TEST SYSTEM

(71) Applicant: WIDEX A/S, Lynge (DK)

(72) Inventors: Francis Kok-Ming Kuk, Lisle, IL (US); Petri Mikael Korhonen, Chicago, IL (US); Bryan Lee Crose, Wheaton, IL (US); Eric Christopher Seper, Orland Park, IL (US); Chi-Chuen Lau, Des Plaines, IL (US)

(73) Assignee: Widex A/S, Lynge (DK)

( * ) Notice: Subject to any disclaimer, the term of this patent is extended or adjusted under 35 U.S.C. 154(b) by 185 days.

(21) Appl. No.: 14/575,411

(22) Filed: Dec. 18, 2014

(65) Prior Publication Data
US 2016/0174880 A1 Jun. 23, 2016

(51) Int. Cl.
*A61B 5/12* (2006.01)
*A61B 5/00* (2006.01)

(52) U.S. Cl.
CPC .............. *A61B 5/123* (2013.01); *A61B 5/742* (2013.01); *A61B 5/7435* (2013.01)

(58) Field of Classification Search
CPC ......... A61B 5/123; A61B 5/121; A61B 5/125; A61B 5/126; A61B 5/128
See application file for complete search history.

(56) References Cited

U.S. PATENT DOCUMENTS

| | | | | |
|---|---|---|---|---|
| 3,408,460 A | * | 10/1968 | Victoreen | A61B 5/12 327/295 |
| 6,447,461 B1 | * | 9/2002 | Eldon | A61B 5/121 600/559 |
| 2011/0299709 A1 | * | 12/2011 | Anderson | A61B 5/121 381/315 |
| 2012/0130271 A1 | * | 5/2012 | Margolis | A61B 5/123 600/559 |
| 2014/0194775 A1 | * | 7/2014 | Van Hasselt | A61B 5/123 600/559 |
| 2015/0025413 A1 | * | 1/2015 | Shennib | A61B 5/123 600/559 |

OTHER PUBLICATIONS

Goldstein, B., and A. Shulman. "Tinnitus-Hyperacusis and the Loudness Discomfort Level Test—A Preliminary Report." The international tinnitus journal 2 (1996): 83-89.*

* cited by examiner

*Primary Examiner* — Sean P Dougherty
*Assistant Examiner* — Nicholas E Kolderman
(74) *Attorney, Agent, or Firm* — Sughrue Mion, PLLC

(57) ABSTRACT

A hearing test system comprising an computerized device (100) having an electro-acoustical output transducer (104) and a graphical user interface (102) and further being adapted to estimate a hearing loss of an individual test person. The invention also relates to a non-transitory computer readable medium carrying instructions which, when executed by a computer, cause a hearing loss of an individual test person to be estimated and a method of estimating a hearing loss.

24 Claims, 1 Drawing Sheet

METHOD OF TESTING HEARING AND A HEARING TEST SYSTEM

The present invention relates to a method of testing hearing. The invention also relates to a hearing test system. Furthermore the invention relates to a non-transitory computer readable medium carrying instructions which, when executed by a computer, cause a hearing loss of an individual test person to be estimated.

BACKGROUND OF THE INVENTION

Generally hearing screening or hearing test methods that allow the hearing loss of an individual to be tested are well known in the art.

Perhaps the most widespread method is based on pure tone tests, where the individual to be tested (i.e. the test person) is presented for a tone at a specific frequency and at first at a very low level that most probably is not audible for the test person, where after the level of the tone is progressively increased until the test person indicates that the tone is audible whereby the hearing threshold may be established, and from that the hearing loss at that specific frequency as compared to normal hearing subjects may be derived. In order to fully characterize the hearing loss the test may be repeated for other frequencies in the audible range.

This type of test has been offered as online test for many years. Hereby individuals that suspect they may have a hearing loss can take the test at home and without having to make an appointment and travel to a hearing care professional.

However, this type of test requires relatively precise calibration of the electro-acoustical output transducer applied by the test person.

Another widespread approach for estimating hearing loss is based on the test person's ability to understand speech. This type of tests is generally known as intelligibility tests. Often interference noise is superposed onto the speech because hearing impaired people often find it particularly difficult to understand speech in noise.

However, this type of test is characterized in that the required feedback from the test person is somewhat more complex than just indicating when a tone is audible because the user feedback typically requires a visual display where a number of words or sentences are given for selection by the user. The methods for estimating a hearing loss based on the achieved intelligibility scores are likewise relatively complex. An additional complexity for this type of test, especially with respect to using them on-line, stems from the fact that they are language dependent. Furthermore this type of test is relatively time consuming.

These types of test are also characterized in that they are quite sensitive to the level of background noise while performing such a test.

It is therefore a feature of the present invention to provide a hearing test system that can provide an improved hearing test.

It is another feature of the present invention to provide a hearing test that is relatively insensitive to calibration of the acoustical output.

It is yet another feature of the present invention to provide a hearing test that is language independent.

It is still another feature of the present invention to provide a hearing test that is simple to carry out for the test person.

It is another feature of the present invention to provide a hearing test that is relatively insensitive to the background noise level while performing such a test.

It is a feature of the present invention to provide a hearing test that may be carried out by the test person in a very short time.

SUMMARY OF THE INVENTION

The invention, in a first aspect, provides a method of testing hearing according to claim 1.

This provides an improved method of testing hearing.

The invention, in a second aspect, provides a hearing test system according to claim 10.

This provides an improved hearing test system.

The invention, in a third aspect, provides a non-transitory computer readable medium according to claim 18.

Further advantageous features appear from the dependent claims.

Still other features of the present invention will become apparent to those skilled in the art from the following description wherein the invention will be explained in greater detail.

BRIEF DESCRIPTION OF THE DRAWINGS

By way of example, there is shown and described a preferred embodiment of this invention. As will be realized, the invention is capable of other embodiments, and its several details are capable of modification in various, obvious aspects all without departing from the invention. Accordingly, the drawings and descriptions will be regarded as illustrative in nature and not as restrictive. In the drawings.

DETAILED DESCRIPTION

Figure 1:
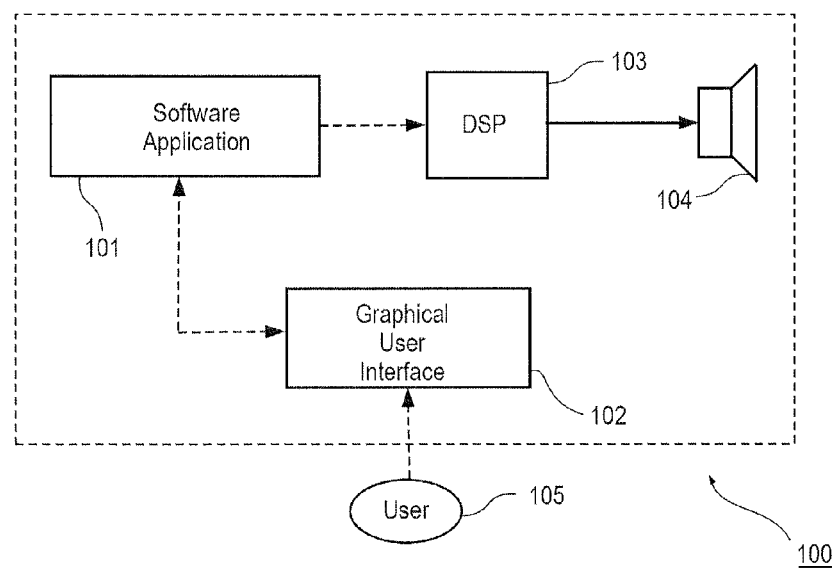
FIG. 1 illustrates highly schematically a computerized device according to an embodiment of the invention.

Within the present context the term software application may be construed to comprise a program storage for storing an executable executable program, and a processor for executing said program. However, the term software application may also be construed to mean a non-transitory computer readable medium carrying instructions that may be executed by a computer.

The inventors have found that the difference between the sound level perceived as most comfortable by the test person (which in the following will be denoted Most-Comfortable-Level (MCL)) and the sound level perceived by the test person as being at the threshold of what the test person can perceive (which in the following will be denoted threshold) can be used to screen for a hearing loss. In the following this difference between MCL and threshold will be denoted Threshold-to-Comfortable-Level Range (TCLR).

The basic premise is that the value of the MCL is tied to the threshold values. It is a specific advantage of the present invention that the difference between the threshold and the MCL is independent on calibration of the sound output provided by the electro-acoustical output transducer of the hearing test system, as long as both threshold and MCL are measured with the same system.

The Table below illustrates how the absolute hearing threshold given in decibel Hearing Loss (dB HL) can be determined based on the measured Threshold-to-Comfortable-Level Range (TCLR), given in dB:

| Absolute Threshold [dB HL] | TCLR [dB] |
|---|---|
| 0 | 60 |
| 10 | 55 |
| 20 | 45 |
| 30 | 40 |
| 40 | 35 |
| 50 | 32 |
| 60 | 28 |
| 70 | 25 |
| 80 | 22 |
| 90 | 20 |
| 100 | 18 |

Thus within the present context a distinction is made between the measured TCLR which is typically given in dB and the determined absolute threshold which is given in dB HL. The relationship given in the table may be considered true for all audible frequencies.

The dB HL is a well known scale within the art of asserting hearing loss and is determined as a sound level relative to the quietest sound level that a young healthy individual ought to be able to hear. In a clinical audiogram test pure tones between say 250 and 8000 Hz are presented at varying sound output levels in order to determine a test person's pure tone detection thresholds (the quietest audible sounds) in the left and right ear. Thresholds between −10 and +20 dB HL are considered in the normal range, while thresholds above say 20 or 25 dB HL are considered to represent at least a mild hearing loss.

It is a specific advantage of the present invention that it is not necessary to know the reference value of the dB scale used to measure the MCL, the threshold and hereby the TCLR because it is only required to know the difference (given in dB) between the two measurements. In other words, it is not necessary to calibrate the sound output level.

According to an embodiment of the invention the hearing test is carried out by downloading a software application from an external server using a computerized device and installing the software on the computerized device. This may especially be attractive in that it allows the test to subsequently be carried out while the computerized device is not connected to the internet.

In variations of the present invention the software application need not be downloaded from the internet but may be transferred to the computerized device from a memory device such as a compact disc. In a further variation the software application may be integrated in a special purpose hearing test device during manufacturing of the special purpose hearing test device. In yet another variation the software application is accommodated on an external server and accessed using an internet browser.

Next the software application is activated by the test person and in response hereto a test signal is provided from the computerized device and the test person is prompted to adjust the level of the test signal, by manipulation of a handle provided by the Graphical User Interface, until the test person perceives the test signal as being at its most comfortable level and storing first data representing that first test signal level using the GUI. In a subsequent step the test person is prompted to adjust the level of the test signal, by manipulation of the handle provided by the GUI, until the test person perceives the level as being barely audible and storing second data representing that second test signal level using the GUI. Then the software application calculates the difference between the levels represented by the first and second data and estimates a hearing loss of the test person by using a look-up table capable of translating the calculated difference into an absolute hearing loss threshold. The table shown above can be used. Thus, assuming a TCLR of 40 dB translates into a hearing loss of 30 dB HL while a TCLR of 22 dB translates into a hearing loss of 80 dB HL. Finally the GUI provides the result of the hearing loss estimation to the test person.

According to the present embodiment the software application prompted the test person to adjust the level of the test signal using a horizontal slider provided by the GUI. No time limit is set with respect to when to store the two selected test signal levels and the test person is therefore able to adjust the slider as many times and for as long as desired.

However, it is a specific advantage of the present embodiment that the hearing loss estimation can be carried out in a very short time. Initial tests have shown that on average it takes a test person less than 30 seconds to complete each TCLR measurement.

In variations any type of handle may be used to adjust the level of the test signal and even a text based interface if a graphical user interface is not provided by the personal computing device.

In a variation of the present embodiment the estimated hearing loss is compared with a threshold value, and in case the estimated hearing loss exceeds the threshold value the test person is diagnosed as having a hearing loss. According to further variations the threshold value is set to a value in the range of 20-30 dB HL, e.g. 25 dB HL.

According to the present embodiment, the acoustical test signal is a warble tone centered at a frequency of 4 kHz. A warble tone is a tone whose frequency varies periodically several times per second over a small frequency range.

According to further variations of the present embodiment the software application may provide the test person with the option to select an alternative or additional acoustical test signal with a tone centered at another frequency in the audible range, such as a center frequency of 500 Hz or 1 kHz.

It is a specific advantage of the present invention that the frequency independence of the relationship between the absolute threshold and TCLR allows the use of a test signal at a relatively high frequency, such as 4 kHz, whereby the accuracy can be improved because the detrimental impact from background noise decreases with increasing frequency due to the fact that most daily situations have more low frequency noise and less high frequency noise.

In case the test person selects to apply a plurality of different acoustical test signals this may be used to provide a more detailed feedback to the test person with respect to the characteristics (i.e. frequency dependence) of her hearing loss or to provide a hearing screening with a higher accuracy.

Reference is first made to FIG. 1, which illustrates highly schematically a computerized device 100 according to an embodiment of the invention. The computerized device 100 comprises a software application 101, a graphical user interface 102, a digital signal processor (DSP) 103 and an electro-acoustical transducer 104.

FIG. 1 illustrates how a test person 105 through the graphical user interface 102 may communicate interactively with the computerized device 100 in a manner controlled by the software application 101. The software application 101 is furthermore adapted to interact with the DSP 103 such that the electro-acoustical transducer 104 can be used to provide a desired acoustical test signal.

Figure 2:
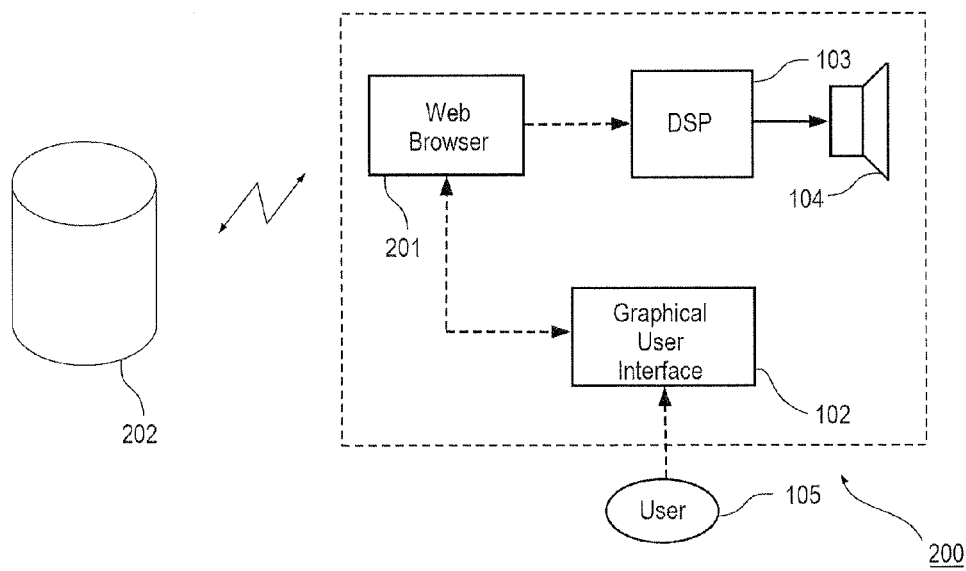
FIG. 2 illustrates highly schematically an external server and a computerized device according to an embodiment of the invention

Reference is now made to FIG. 2, which illustrates highly schematically a computerized device 200 and an external server 202 according to an embodiment of the invention. The computer device 200 comprises basically the same elements as the computer device 100 from the embodiment of FIG. 1, except that the functionality that in the embodiment of FIG. 1 is provided by the software application 101, in the embodiment of FIG. 2 instead is provided by a web service, that is hosted on the external server 202 and may be accessed using the web browser 201.

In variations of the present embodiment the computerized device may be a smart phone, a tablet computer, a portable personal computer or a stationary personal computer. According to the embodiments of FIG. 1 and FIG. 2 the electro-acoustical transducer 104 is a traditional loudspeaker. However, the loudspeaker provides the acoustical test signal to both ears simultaneously, which may be less advantageous in some cases, e.g. if the person only has a hearing deficit in one ear. In variations the software application is therefore set up to provide an acoustical test signal that is selectively provided to either the left ear or the right ear using a set of standard headphones or earphones connected to the computerized device.

The invention claimed is:

1. A method of estimating hearing loss using a computerized device having an electro-acoustical output transducer and a graphical user interface, the method comprising the steps of:
    providing from said electro-acoustical output transducer an acoustical test signal that is a warble tone,
    prompting a test person to adjust a level of the test signal, by manipulation of a handle provided by the graphical user interface, until the test person perceives the test signal as being at the test signal's most comfortable level,
    storing first data representing the test signal level that the test person perceives as the most comfortable,
    prompting the test person to adjust the level of the test signal, by manipulation of the handle provided by the graphical user interface, until the test person perceives the test signal as being barely audible,
    storing second data representing the test signal level that the test person perceives as being barely audible,
    calculating a difference between the test signal levels represented by the first and second data, to thereby provide a measure in dB of the difference that is independent of calibration of the sound output provided by the electro-acoustical output transducer,
    estimating a hearing loss of the user as an absolute hearing loss in dB HL based on the calculated difference, and
    providing a result of the hearing loss estimation to the user.

2. The method according to claim 1, wherein the step of providing the result of the hearing loss estimation to the user comprises the further steps of:
    comparing the hearing loss estimation with a threshold value,
    diagnosing the user as having a hearing loss in case the hearing loss estimation exceeds the threshold value.

3. The method according to claim 1, wherein the step of estimating the hearing loss of the user based on the calculated difference comprises the further steps of:
    using a look-up table to translate the calculated difference into the hearing loss estimation.

4. The method according to claim 1, wherein the step of providing the result of the hearing loss estimation to the user comprises the further steps of:
    comparing the calculated difference with a threshold value selected from a range between 50 and 40 dB,
    diagnosing the user as having a hearing loss in case the calculated difference is below said threshold value.

5. The method according to claim 1, wherein the acoustical test signal has a center frequency in a range between 3 kHz and 5 kHz.

6. The method according to claim 1, wherein the computerized device is a smart phone, tablet computer, portable personal computer or stationary personal computer.

7. The method according to claim 1, wherein a software application is adapted to be downloaded from an external server and subsequently may be executed independently of the external server.

8. The method according to claim 1, wherein a software application is adapted to be executed at least partly from an external server and adapted to be accessed using a web browser of the computerized device.

9. A hearing test system comprising a computerized device having an electro-acoustical transducer, a graphical user interface, a program storage for storing an executable program, and a processor for executing said program to perform the following method comprising the steps of:
    providing from said electro-acoustical transducer an acoustical test signal that is a warble tone,
    prompting a test person to adjust a level of the test signal, by manipulation of a handle provided by the graphical user interface, until the test person perceives the test signal as being at the test signal's most comfortable level,
    storing first data representing the test signal level that the test person perceives as the most comfortable,
    prompting the test person to adjust the level of the test signal, by manipulation of the handle provided by the graphical user interface, until the test person perceives the test signal as being barely audible,
    storing second data representing the test signal level that the test person perceives as being barely audible,
    calculating a difference between the test signal levels represented by the first and second data, to thereby provide a measure in dB of the difference that is independent of calibration of the sound output provided by the electro-acoustical output transducer,
    estimating a hearing loss of the user as an absolute hearing loss in dB HL based on the calculated difference, and
    providing a result of the hearing loss estimation to the user.

10. The hearing test system according to claim 9, wherein the step of providing the result of the hearing loss estimation to the user comprises the further steps of:
    comparing the hearing loss estimation with a threshold value,
    diagnosing the user as having a hearing loss in case the hearing loss estimation exceeds the threshold value.

11. The hearing test system according to claim 9, wherein the step of estimating the hearing loss of the user based on the calculated difference comprises the further steps of:
    using a look-up table to translate the calculated difference into the hearing loss estimation.

12. The hearing test system according to claim 9, wherein the step of providing the result of the hearing loss estimation to the user comprises the further steps of:

comparing the calculated difference with a threshold value that is selected from a range between 50 and 40 dB, diagnosing the user as having a hearing loss in case the calculated difference is below the threshold value.

13. The hearing test system according to claim 9, wherein the acoustical test signal has a center frequency in a range between 3 kHz and 5 kHz.

14. The hearing test system according to claim 9, wherein the computerized device is a smart phone, tablet computer, portable personal computer or stationary personal computer.

15. The hearing test system according to claim 9, wherein a software application is adapted to be downloaded from an external server and subsequently may be executed independently of the external server.

16. The hearing test system according to claim 9, wherein a software application is adapted to be executed at least partly from an external server and adapted to be accessed using a web browser of the computerized device.

17. A non-transitory computer readable medium carrying instructions which, when executed by a computer, cause the following method to be performed, the method comprising the steps of:

providing from an electro-acoustical output transducer an acoustical test signal that is a warble signal, prompting a test person to adjust a level of the test signal, by manipulation of a handle provided by a graphical user interface, until the test person perceives the test signal as being at the test signal's most comfortable level, storing first data representing the test signal level that the test person perceives as the most comfortable, prompting the test person to adjust the level of the test signal, by manipulation of the handle provided by the graphical user interface, until the test person perceives the test signal as being barely audible, storing second data representing the test signal level that the test person perceives as being barely audible, calculating a difference between the test signal levels represented by the first and second data, to thereby provide a measure in dB of the difference that is independent of calibration of the sound output provided by the electro-acoustical output transducer, estimating a hearing loss of the user as an absolute hearing loss in dB HL based on the calculated difference, and providing a result of the hearing loss estimation to the user.

18. The non-transitory computer readable medium according to claim 17, wherein the step of providing the result of the hearing loss estimation to the user comprises the further steps of:

comparing the hearing loss estimation with a threshold value, diagnosing the user as having a hearing loss in case the hearing loss estimation exceeds the threshold value.

19. The non-transitory computer readable medium according to claim 17, wherein the step of estimating the hearing loss of the user based on the calculated difference comprises the further steps of:

using a look-up table to translate the calculated difference into the hearing loss estimation.

20. The non-transitory computer readable medium according to claim 17, wherein the step of providing the result of the hearing loss estimation to the user comprises the further steps of:

comparing the calculated difference with a threshold value that is selected from a range between 50 and 40 dB, diagnosing the user as having a hearing loss in case the calculated difference is below the threshold value.

21. The non-transitory computer readable medium according to claim 17, wherein the acoustical test signal has a center frequency in a range between 3 kHz and 5 kHz.

22. The non-transitory computer readable medium according to claim 17, wherein the computer is a smart phone, tablet computer, portable personal computer or stationary personal computer.

23. The non-transitory computer readable medium according to claim 17, wherein a software application is adapted to be downloaded from an external server and subsequently may be executed independently of the external server.

24. The non-transitory computer readable medium according to claim 17, wherein a software application is adapted to be executed at least partly from an external server and adapted to be accessed using a web browser of the computer.

* * * * *